United States Patent
Yoo

(10) Patent No.: US 11,633,169 B2
(45) Date of Patent: Apr. 25, 2023

(54) APPARATUS FOR AI-BASED AUTOMATIC ULTRASOUND DIAGNOSIS OF LIVER STEATOSIS AND REMOTE MEDICAL DIAGNOSIS METHOD USING THE SAME

(71) Applicant: HEALCERION CO., LTD., Seoul (KR)

(72) Inventor: Jae Chern Yoo, Gyeonggi-do (KR)

(73) Assignee: HEALCERION CO., LTD., Gyeonggi-do (KR)

(*) Notice: Subject to any disclaimer, the term of this patent is extended or adjusted under 35 U.S.C. 154(b) by 806 days.

(21) Appl. No.: 16/665,243

(22) Filed: Oct. 28, 2019

(65) Prior Publication Data
US 2020/0367853 A1 Nov. 26, 2020

(30) Foreign Application Priority Data
May 20, 2019 (KR) .................. 10-2019-0059049

(51) Int. Cl.
| | |
|---|---|
| A61B 8/00 | (2006.01) |
| A61B 8/08 | (2006.01) |
| G06T 7/11 | (2017.01) |
| G16H 50/20 | (2018.01) |
| G16H 80/00 | (2018.01) |
| G16H 70/20 | (2018.01) |
| G16H 30/40 | (2018.01) |

(Continued)

(52) U.S. Cl.
CPC ............ *A61B 8/085* (2013.01); *A61B 5/7267* (2013.01); *A61B 8/4472* (2013.01); *A61B 8/463* (2013.01); *A61B 8/5246* (2013.01); *A61B 8/565* (2013.01); *G06T 7/0014* (2013.01); *G06T 7/11* (2017.01); *G16H 30/40* (2018.01); *G16H 50/20* (2018.01); *G16H 70/20* (2018.01); *G16H 80/00* (2018.01); *G06T 2207/10132* (2013.01); *G06T 2207/20081* (2013.01); *G06T 2207/20084* (2013.01); *G06T 2207/20221* (2013.01); *G06T 2207/30056* (2013.01)

(58) Field of Classification Search
CPC combination set(s) only.
See application file for complete search history.

(56) References Cited

U.S. PATENT DOCUMENTS

2018/0144243 A1* 5/2018 Hsieh .................. G06F 30/20

FOREIGN PATENT DOCUMENTS

EP 2140412 B1 12/2018

OTHER PUBLICATIONS

Byra, M., et al.; "Transfer learning with deep convolutional neural network for liver steatosis assessment in ultrasound images", International Journal of Computer Assisted Radiology and Surgery (2018) 13:1895-1903.

(Continued)

*Primary Examiner* — Joel F Brutus
(74) *Attorney, Agent, or Firm* — Harness, Dickey & Pierce, P.L.C.

(57) ABSTRACT

Disclosed herein are an apparatus for AI-based automatic ultrasound diagnosis of liver steatosis and a remote medical diagnosis method using the same applied in the field of ultrasound image processing. The apparatus for AI-based automatic ultrasound diagnosis of liver steatosis can automatically determine a grade of liver steatosis, which is difficult to determine visually, through extraction from an image acquired by imaging medical examination using a deep learning trained artificial neural network.

5 Claims, 9 Drawing Sheets

(51) Int. Cl.
*A61B 5/00* (2006.01)
*G06T 7/00* (2017.01)

(56) References Cited

OTHER PUBLICATIONS

Marshall, R. H., et al.; "Hepatorenal Index as an Accurate, Simple, and Effective Tool in Screening for Steatosis", AJR 2012; 199:997-1002.
Szegedy, C., et al.; "Going Deeper with Convolutions", 2015, Computer Vision and Pattern Recognition, pp. 1-9.
Szegedy, C., et al.; "Rethinking the Inception Architecture for Computer Vision", 2016, Computer Vision and Pattern Recognition, pp. 1-9.
Chen, L. C., et al.; "Rethinking Atrous Convolution for Semantic Image Segmentation", 2017, Computer Vision and Pattern Recognition, pp. 1-14.

* cited by examiner

APPARATUS FOR AI-BASED AUTOMATIC ULTRASOUND DIAGNOSIS OF LIVER STEATOSIS AND REMOTE MEDICAL DIAGNOSIS METHOD USING THE SAME

CROSS-REFERENCE TO RELATED APPLICATION

This application claims the benefit of and priority to Korean Patent Application 10-2019-0059049, filed May 20, 2019, the entire disclosure of which is incorporated herein by reference.

FIELD

The present invention relates to an apparatus for AI-based automatic ultrasound diagnosis of liver steatosis which can automatically determine a grade of liver steatosis, which is difficult to determine visually, through extraction from an image acquired by imaging medical examination using a deep learning-trained artificial neural network, and a remote medical diagnosis method using the same. More particularly, the present invention relates to an apparatus for AI-based automatic ultrasound diagnosis of liver steatosis which detects a liver region and a kidney region required for diagnosis of liver steatosis from an ultrasound image, concatenates and combines images of the two regions into one integrated image, decomposes the integrated image into four sub-band images, that is, an LL image, an LH image, an HL image, and an HH image, by discrete wavelet transform, trains independent artificial neural networks on the respective sub-band images, and automatically determines a grade of liver steatosis in the patient based on the ultrasound image of the patient received from an ultrasound probe sensor using the deep learning-trained artificial neural networks, and a remote medical diagnosis method using the same.

In addition, the present invention is advantageously used in implementing a virtual doctor that automatically analyzes the degree of liver steatosis in a patient using a deep learning-trained AI platform, notifies the patient or a doctor of an analysis result, and provides a remote consultation service via the Internet.

BACKGROUND

This application is a continuation of an earlier-issued European patent titled "Remote Medical-Diagnosis System and Method" (issued on Dec. 12, 2018, Patent Ser. No. 02/140,412).

The earlier-issued patent discloses a remote medical diagnosis system and a remote medical diagnosis method using the same, the remote medical diagnosis system including: a bioanalyzer including a bio-disc or a lab-on-a-disc adapted to receive a sample therein to perform a biological, chemical or biochemical reaction; a virtual doctor including a medical examination device including a thermometer, a sphygmomanometer, a camera, a stethoscope, a body fat analyzer, a vascular screening device, an ultrasound imager, a urinalysis device, a pulsimeter, a blood collection device, an electrocardiographer, an X-ray device, an oxygen saturation tester, a dementia testing device, a computerized axial tomographer (CAT), a magnetic resonance imager (MRI), a capsule endoscope, a magnifier, a camera-integrated magnifier, and a bioshirt having a function of measuring biological signals (diabetes, obesity, blood pressure, pulse, electrocardiogram, body temperature, and the like), the virtual doctor residing as software in a user terminal to guide or instruct how to use the bioanalyzer and the medical examination device and provide a consultation service with a user; a user terminal providing a consultation service with a medical expert or the virtual doctor; a medical expert terminal providing a consultation service with a user; and a remote diagnosis server connecting a user to a medical expert as a consultation specialist during a regular medical check-up period, connecting a user to the virtual doctor during the other periods, and blocking connection between the user and the virtual doctor if the regular medical check-up period elapses without consultation with the medical expert.

Recently, as digital image processing technology has been used in the field of clinical diagnosis along with medical device manufacturing technology, there have been many advances in diagnostic radiology.

In particular, ultrasound diagnosis is thus harmless to the human body by allowing avoidance of exposure to harmful radiation, as compared with CT or X-ray medical equipment, allows acquisition of a cross-sectional image of the human body in a non-invasive manner, and is portable and inexpensive. Particularly, ultrasound diagnosis allows real-time image acquisition and thus real-time observation of movement of an organ.

Such an ultrasound diagnostic technique is widely used to determine the degree of liver steatosis using the fact that reflection properties of ultrasound waves significantly differ between water and fat.

Fatty liver is the most common disease and is detected by abdominal ultrasonography. Recently, diagnosis of liver steatosis is mainly carried out by measuring the brightness level or texture properties of an abdominal cross-sectional image obtained by ultrasound equipment and calculating a hepatorenal sonographic index (HI), which is a measure for determining the degree of steatosis in liver tissue, wherein the HI is generally a ratio of mean brightness level or degree of texture between a liver and a right kidney on an echogenicity histogram of a cortex. However, diagnosis of fatty liver based on the hepatorenal sonographic index (HI) obtained using the brightness level or the texture characteristics of an ultrasound image has a problem in that calculation errors are likely to occur due to low resolution of the ultrasound image and severe noise. In addition, the ultrasound image is often severely damaged, causing difficulty in accurate medical interpretation by nonprofessionals. Further, fatty liver is divided into four grades: normal, mild, moderate, and severe, and, in more severe cases, may be diagnosed as liver cirrhosis or liver cancer.

Inaccuracy of calculation of the HI leads to increase in ambiguity of determination of the fatty liver grade using ultrasound examination and, eventually, the determination depends on subjective judgment of an examiner, causing inconsistency between opinions of different examiners and confusion in reading results of ultrasound examination.

The present invention has been conceived to solve such problems in the art and provides an apparatus for AI-based automatic ultrasound diagnosis of liver steatosis which extracts images of a liver region and a kidney region, concatenates and combines the images of the two regions into one integrated image, performs discrete wavelet transform on the integrated image to acquire sub-band images, trains artificial neural networks on the respective sub-band images, and automatically determines a grade of liver steatosis in a patient using the deep learning-trained artificial neural networks, and a remote medical diagnosis method using the same.

RELATED LITERATURE

Patent Document (Patent document 0001) European Patent No. 02140412 (issued on Dec. 12, 2018)

Non-Patent Document (Non-patent document 0001) (Article 1) Michal Byra and Grzegorz Styczynski, et al, "Transfer learning with deep convolutional neural network for liver steatosis assessment in ultrasound images", International Journal of Computer Assisted Radiology and Surgery, August, 2018

(Non-patent Document 0002) (Article 2) Marshall R H, Eissa M, Bluth E I, Gulotta P M, Davis N K "Hepatorenal index as an accurate, simple, and effective tool in screening for steatosis" American Journal of J Roentgenology Vol. 199 (2012), pp. 997-1002

(Non-patent Document 0003) (Article 3) Christian Szegedy et al., Going Deeper with Convolutions, 2015 Computer Vision and Pattern Recognition (Non-patent Document 0004) (Article 4) Christian Szegedy et al., Rethinking the Inception Architecture for Computer Vision, 2016 Computer Vision and Pattern Recognition (Non-patent Document 0005) (Article 5) Liang-Chieh Chen et al., Rethinking Atrous Convolution for Semantic Image Segmentation, 2017 Computer Vision and Pattern Recognition

SUMMARY

The present invention has been conceived to solve such problems in the art and it is one aspect of the present invention to provide an apparatus for AI-based automatic ultrasound diagnosis of liver steatosis which can automatically screen liver steatosis based on an ultrasound image of a patient using artificial intelligence (AI), the apparatus for AI-based automatic ultrasound diagnosis of liver steatosis detecting a liver region and a kidney region required for diagnosis of liver steatosis from the ultrasound image, concatenating and combining images of the two regions into one integrated image, decomposing the integrated image into four sub-band images, that is, an LL image, an LH image, an HL image, and an HH image by discrete wavelet transform, training independent artificial neural networks on the respective sub-band images, and automatically determining a grade of liver steatosis in the patient based on the ultrasound image of the patient received from an ultrasound image sensor using the deep learning-trained artificial neural networks.

It is another aspect of the present invention to provide a remote medical diagnosis method which automatically analyzes liver steatosis in a patient using the apparatus for AI-based automatic ultrasound diagnosis of liver steatosis set forth above, notifies the patient or a doctor of an analysis result via the Internet, and provides a consultation service with a medical expert using a virtual doctor further provided.

However, it should be understood that the technical problem to be solved by embodiments of the present invention is not limited to the aforementioned technical problems and other technical problems may exist.

In accordance with one aspect of the present invention, an apparatus for AI-based automatic ultrasound diagnosis of liver steatosis includes: an ultrasound probe sensor acquiring an ultrasound image from a patient; a region-of-interest extraction unit acquiring images of one or more regions of interest helpful to diagnosis of liver steatosis from the ultrasound image; an image integration unit concatenating the images of the one or more regions of interest into one integrated image; a darkness-to-shape transform kernel transforming the integrated image into a shape-based integrated image; and an artificial neural network trained on the shape-based integrated image by deep learning, wherein the deep learning-trained artificial neural network automatically determines a grade of liver steatosis in the patient based on the ultrasound image of the patient received from the ultrasound probe sensor.

In accordance with another aspect of the present invention, an apparatus for AI-based automatic ultrasound diagnosis of liver steatosis includes: an ultrasound probe sensor acquiring an ultrasound image from a patient; a region-of-interest extraction unit acquiring images of one or more regions of interest helpful to diagnosis of liver steatosis from the ultrasound image; an image integration unit including a rearrangement unit rearranging image pixels of each of the images of the regions of interest acquired by the region-of-interest extraction unit to obtain a pattern image, the image integration unit concatenating the pattern images into one integrated image; and an artificial neural network trained on the integrated image by deep learning, wherein the deep learning-trained artificial neural network automatically determines liver steatosis in the patient based on the ultrasound image of the patient received from the ultrasound probe sensor.

The artificial neural network according to the present invention may be a convolutional neural network (CNN) or a recurrent neural network (RNN).

In the present invention, the artificial neural network is a neural network that can be trained by deep learning, and may include at least one layer or element selected from the group of a convolution layer, a pooling layer, an ReLu layer, a transpose convolution layer, an unpooling layer, a 1×1 convolutional layer, a skip connection, a global average pooling (GAP) layer, a fully connected layer, a long short term memory (LSTM), a softmax classifier, an auxiliary classifier, and a support vector machine (SVM). For example, the artificial neural network may be an artificial neural network which further includes an operation unit for batch normalization upstream of the ReLu layer.

The region-of-interest extraction unit may set a region of interest for ultrasound diagnosis for a patient on the ultrasound image using a rectangular or elliptical window to extract an image sample within a region of the window.

Accordingly, only darkness intensity of pixels within the window differs between the extracted images of the regions of interest depending on the degree of liver steatosis in a patient, and the extracted images all have a rectangular or elliptical shape, which corresponds to the shape of the window.

That is, although fatty liver is classified into four grades, that is, normal, mild, moderate, and severe, based on the degree of steatosis, the extracted images of the regions of interest have the same outer shape regardless of the grade of fatty liver. In other words, only the darkness intensity of pixels within the window differs between the extracted images depending on the grade of fatty liver, and outer shapes of the extracted images are identical to the shape of the window used.

In addition, different integrated images, which are acquired by combining the images of several regions of interest into one, have a uniform outer shape. That is, since integrated images indicative of different fatty liver grades have the same outer shape, it is impossible to determine the grade of fatty liver based on the outer shape of the integrated image. In other words, integrated images indicative of different fatty liver grades differ only in darkness intensity of pixels therein.

Unfortunately, known artificial neural networks are designed to learn and recognize an outer shape of an image, rather than darkness intensity of image pixels.

For example, the reason why existing artificial neural networks distinguish a car from a cat is that the two objects have different outer shapes. Since the extracted integrated images have the same outer shape despite being indicative of different fatty liver grades, it is very difficult for existing artificial neural networks to efficiently learn and recognize the images.

In order to solve this problem, the apparatus according to the present invention includes the darkness-to-shape transform kernel transforming the darkness intensity-based image into a shape-based image. The darkness-to-shape transform kernel transforms a lower-dimensional image into a higher-dimensional image to generate an image having an outer shape that varies depending on data of darkness intensity of pixels. In the present invention, an image obtained through transformation by the darkness-to-shape transform kernel depending on data of darkness intensity of pixels in an image obtained by the region-of-interest extraction unit is referred to as "shape-based image".

In addition, an image upstream of the darkness-to-shape transform kernel is referred to as "darkness intensity-based image".

The darkness-to-shape transform kernel transforms the darkness intensity-based image into the shape-based image.

For example, suppose that an image extracted from a first patient by the region-of-interest extraction unit is indicative of normal liver steatosis and an image extracted from a second patient by the region-of-interest extraction unit is indicative of severe liver steatosis. Since all regions of interest in the ultrasound images were extracted using a predetermined window at the time of extraction, the extracted images have the same outer shape, which corresponds to the shape of the window. Therefore, it is not only difficult to distinguish between liver steatosis grades of the two patients based on the outer shapes of the extracted images, but it is also difficult for an artificial neural network to efficiently learn and recognize the extracted images.

However, since the distribution and pattern of darkness intensity of pixels significantly differ between the darkness intensity-based images extracted from the two patients, shape-based images having different outer shapes can be obtained through transformation of the darkness intensity-based images by the darkness-to-shape transform kernel. Since the shape-based images have different outer shapes, the artificial neural network can efficiently learn and recognize the shape-based images.

The darkness-to-shape transform kernel may be any one selected from the group of a linear kernel, a polynomial kernel, a Gaussian kernel, a hyperbolic tangent kernel, and a radial basis function (RBF) kernel, which are well known to those skilled in the art.

Preferably, the darkness-to-shape transform kernel is a polynomial kernel given by the following equation:

$$(x_1, x_2) \rightarrow (x_1^2, \sqrt{2}x_1x_2, x_2^2)$$

On the left side of the equation, $x_1$ may denote an address of each pixel in a darkness intensity-based image and $x_2$ may denote darkness intensity of the pixel.

The darkness-to-shape transform kernel transforms the darkness intensity-based image given by $(x_1, x_2)$ in the left side of the equation into a shape-based image expressed by $(x_1^2, \sqrt{2}x_1x_2, x_2^2)$ in the right side of the equation.

Here, the shape-based image is displayed in a three-dimensional space and is expressed by darkness intensity at a location in a two-dimensional plane. For example, $x_1^2$ may denote a coordinate value on the horizontal axis in the two-dimensional plane, $\sqrt{2}x_1x_2$ may denote a coordinate value on the vertical axis in the two-dimensional plane, and $x_2^2$ may denote darkness intensity of a pixel at a location represented by the coordinate value on the horizontal axis and the coordinate value on the vertical axis.

In another embodiment, the shape-based image may be displayed in a three-dimensional space and may be represented by darkness intensity in a two-dimensional plane, wherein $x_1^2$ may denote a coordinate value on the horizontal axis in the two-dimensional plane, $x_2^2$ may denote a coordinate value on the vertical axis in the two-dimensional plane, and $\sqrt{2}x_1x_2$ may denote darkness intensity of a pixel at a location represented by the coordinate value on the horizontal axis and the coordinate value on the vertical axis.

In addition, $x_1$, which denotes the address of each pixel in the darkness intensity-based image, may be a serial number assigned to the pixel.

For example, if the region-of-interest extraction unit uses a rectangular window to extract a region of interest from an ultrasound image and the size of the window is set to 3×3, $x_1$ is a number between 1 and 9 since the total number of pixels is 9.

In addition, if an ultrasound image having 256 gray levels is used, $x_2$, which represents darkness intensity of each pixel in a region of interest of the ultrasound image, is a number between 0 and 255.

In another embodiment, $x_1$ may be the sum of the x-axis and y-axis coordinate values of each pixel.

The image integration unit according to the present invention may further include a rearrangement unit that receives a first image, a second image, a kidney border image, and a third image from the region-of-interest extraction unit, the first image being obtained by extracting a region including a kidney and a liver from the ultrasound image, the second image being obtained by extracting only a kidney region from the first image, the kidney border image being obtained by extraction along a boundary between the first image and the second image, and the third image being obtained by extracting the remaining portion of the first image excluding the second image and the kidney border image; generates a pattern image of the second image by taking image pixels from the second image while circularly moving starting from center coordinates of the second image and rearranging the taken image pixels into a rectangular image; generates a pattern image of the kidney border image taking image pixels from the kidney border image while circularly moving along the kidney border image and rearranging the taken image pixels into a rectangular image; and generates a pattern image of the third image by taking image pixels from the third image according to a predetermined pixel scanning scheme and rearranging the taken images into a rectangular image. The image integration unit concatenates the generated pattern images into one integrated image.

Since image patterns in the pattern image of the second image, the pattern image of the kidney border image, and the pattern image of the third image significantly differ between different liver steatosis grades, the artificial neural network can efficiently learn and recognize the integrated image.

In one embodiment, the pixel scanning scheme may be set such that the rearrangement unit takes image pixels from the third image while moving from left to right and from top to bottom of the third image.

In another embodiment, the pixel scanning scheme may be set such that the rearrangement unit takes image pixels from the third image while circularly rotating in a direction of increasing radius from an inside of the third image.

In accordance with a further aspect of the present invention, an apparatus for AI-based automatic ultrasound diagnosis of liver steatosis includes: an ultrasound probe sensor acquiring an ultrasound image from a patient; a region-of-interest extraction unit obtaining images of one or more regions of interest from the ultrasound image; an image integration unit combining the images of the one or more regions of interest into one integrated image; a wavelet transform unit decomposing the integrated image into sub-band images by discrete wavelet transform; and an artificial neural network trained on the sub-band images by deep learning, wherein the deep learning-trained artificial neural network automatically determines a grade of liver steatosis in the patient based on the ultrasound image of the patient received from the ultrasound probe sensor.

In another embodiment, the apparatus for AI-based automatic ultrasound diagnosis of liver steatosis may further include a darkness-to-shape transform kernel transforming the sub-band images into one shape-based sub-band image, wherein the artificial neural network may be trained on the shape-based sub-band image by deep learning.

The region-of-interest extraction unit may extract at least two selected from the group of an image of a liver parenchyma region, an image of a kidney parenchyma region, an image of a right portal vein (RPV) region, an image of a hepatic vein region, an image of a kidney region, an image of a spleen region, and an image of a diaphragm region from the ultrasound image.

In the present invention, the discrete wavelet transform unit may decompose a two-dimensional ultrasound image into four sub-band images, that is, an LL image, an LH image, an HL image, and an HH image, by applying a low pass filter and a high pass filter in a horizontal or vertical direction of a two-dimensional ultrasound image, followed by downsampling by a factor of 2.

Here, the sub-band LL image is acquired by applying the low pass filter in both horizontal and vertical directions of an original ultrasound image, followed by subsampling by a factor of ½ in each of the horizontal and vertical directions.

The sub-band HL image is acquired by applying the low pass filter and the high pass filter in the horizontal and vertical directions of the original ultrasound image, respectively, followed by subsampling by a factor of ½ in each of the horizontal and vertical directions.

The sub-band LH image is acquired by applying the high pass filter and the low pass filter in the horizontal and vertical directions of the original ultrasound image, respectively, followed by subsampling by a factor of ½ in each of the horizontal and vertical directions.

The sub-band HH image is acquired by applying the high pass filter in both the horizontal and vertical directions of the original ultrasound image, followed by subsampling by a factor of ½ in each of the horizontal and vertical directions.

In another embodiment, the darkness-to-shape transform kernel unit may transform each of the four sub-band images into a shape-based sub-band image to generate a shape-based sub-band LL image, a shape-based sub-band LH image, a shape-based sub-band HL image, and a shape-based sub-band HH image, and the artificial neural network may include a first artificial neural network trained on the shape-based sub-band LL image, a second artificial neural network trained on the shape-based sub-band LH image, a third artificial neural network trained on the shape-based sub-band HL image, and a fourth artificial neural network trained on the shape-based sub-band HH image.

In the present invention, the organ of interest may include a liver, a right portal vein (RPV), a hepatic vein, a kidney, a spleen, and a diaphragm, and the ultrasound image may be an ultrasound image obtained by placing the ultrasound probe sensor in a parasagittal scan plane with respect to an affected area. Preferably, the organ of interest includes a liver and a kidney.

In another embodiment, the region-of-interest extraction unit may include an artificial neural network performing semantic segmentation on the ultrasound image to acquire a semantic segmented ultrasound image in which different organs of interest are labeled with different values or different colors for extraction of the images of the regions of interest. The region-of-interest extraction unit may generate a first image by extracting a region including the kidney and the liver among the organs of interest from the ultrasound image by semantic segmentation, generate a second image by extracting only a kidney region from the first image by semantic segmentation, generate a kidney border image by extraction along a boundary between the first image and the second image, generate a third image by extracting the remaining portion of the first image excluding the second image and the kidney border image, and transmit the second image, the kidney border image, and the third image to the image integration unit.

Here, the rearrangement unit of the image integration unit may generate a pattern image of the second image by taking image pixels from the second image while circularly moving starting from center coordinates of the second image and rearranging the taken image pixels into a rectangular image; generate a pattern image of the kidney border image taking image pixels from the kidney border image while circularly moving along the kidney border image and rearranging the taken image pixels into a rectangular image; and generate a pattern image of the third image by taking image pixels from the third image according to a predetermined pixel scanning scheme and rearranging the taken images into a rectangular image. The image integration unit concatenates the generated pattern images into one integrated image.

Semantic segmentation may be performed using an artificial neural network that detects a location of an organ corresponding to a specific class in a given ultrasound image by object classification on a pixel-by-pixel basis and separates the organ from the other organs, provided that the organ is present in the ultrasound image.

The semantic segmented ultrasound image may be a color map of organs which is configured by preassigning different colors to different organs.

For example, the color map may be configured by assigning green to a liver, yellow to a kidney, blue to a spleen, and orange to a diaphragm, Here, semantic segmentation may be performed based on color.

In a further embodiment, the region-of-interest extraction unit may include: a feature point detection unit detecting a feature point in the ultrasound image; a reference feature point storage unit storing a feature point of a reference organ image; and an organ matching unit finding an organ of interest from the ultrasound image through an organ matching process that compares similarity between the feature point detected by the feature point detection unit and the feature point of the reference organ image stored in the reference feature point storage unit. The region-of-interest extraction unit according to this embodiment may generate a first image by extracting a region including the kidney and the liver among the organs of interest from the ultrasound image, generate a second image by extracting only a kidney region from the first image, generate a kidney border image by extraction along a boundary between the first image and the second image, and generate a third image by extracting the remaining portion of the first image excluding the second image and the kidney border image.

The reference organ image may include images of the organs of interest such as the liver, the kidney, the spleen, and the diaphragm, which are acquired from an image indicative of normal liver steatosis. In the organ matching process, locations of the organs of interest in an ultrasound image are detected based on the feature point of the reference organ image.

The organ matching process may be performed using only selected pixels such as feature points (key points). Specifically, the organ matching process may be performed by finding feature points in two or more images, such as a point, line, border, or edge component, and matching the feature points to one another. A corner point may be used as the feature point.

The corner point may include pixels which can be easily identified even when the shape, size, or position of an object changes and locations of which can be easily detected in an image even when illumination of a camera changes. Specifically, the corner point may be a pixel that causes significant changes to an image in all directions (in vertical, horizontal and diagonal directions) when a small predetermined window movable vertically and laterally is shifted on the image while gradually scanning the image.

Examples of an algorithm for extracting the corner point or the feature point may include Harris corner detection, scale-invariant feature transform (SIFT), speeded-up robust features (SURF) and features from accelerated segment test (FAST), which are well known to those skilled in the art.

In the present invention, a small image acquired by collecting pixels around a feature point of an ultrasound image to be matched is referred to as a "patch image".

In the present invention, the feature point of the reference organ image is referred to as "reference feature point" and the feature point of the patch image is referred to as "matching feature point". The organ matching process includes a process of matching the matching feature point to the reference feature point by geometric transformation. Geometric transformation includes translation, rotation, and scaling in a coordinate space.

In the present invention, after comparing similarity between feature points of two images (the reference organ image and the patch image) and performing geometric transformation, a cross-correlation coefficient between the two images may be calculated. If the cross-correlation coefficient is high, it is determined that a corresponding organ is located in the patch image.

That is, the feature point of the reference organ image is compared with the feature point of each patch image to select a patch image having a feature point with high similarity to the reference feature point, thereby generating a pair of feature points between the two images (the reference organ image and the selected patch image). Then, a correspondence between the feature points in the two images is ascertained to determine a geometric transformation relation between the two images. Then, the patch image is aligned with the reference organ image by geometric transformation based on the determined geometric transformation relation, followed by calculating a cross-correlation coefficient between the two images (the reference organ image and the geometrically transformed patch image). If the cross-correlation coefficient between the two images is greater than a predetermined threshold, it is determined that a corresponding organ is located in a current patch image in the ultrasound image.

Each of the feature points may contain data of the coordinate location and orientation thereof. Using these data, the geometric transformation relation between the two images (the reference organ image and the patch image) may be determined based on the pair of feature points between the two images.

The orientation data may be calculated based on gradient direction and magnitude calculated from pixels around the feature point.

The cross-correlation coefficient may be calculated using any one selected from the group of sum of squared difference (SSD), sum of absolute difference (SAD), k-nearest neighbor algorithm (KNN), and normalized cross correlation (NCC).

In yet another embodiment, the region-of-interest extraction unit may detect and extract a location of an organ of interest in the ultrasound image through wavelet frame or redundant (over-complete) wavelet-based organ matching.

In wavelet frame or redundant (over-complete) wavelet-based organ matching, an overlapping pixel determination unit may be used to select overlapping pixels between a sub-band HL frame image, a sub-band LH frame image, and a sub-band HH frame image acquired by wavelet frame transform of the ultrasound image as the feature point (key point or corner point).

The overlapping pixels may be pixels having a value greater than a feature point determination threshold, wherein the pixels are found by performing pixel-by-pixel multiplication between the sub-band HL frame image, the sub-band LH frame image, and the sub-band HH frame image acquired by wavelet frame transform of the ultrasound image, followed by application of the feature point determination threshold on a pixel-by-pixel basis. The overlapping pixels may be used as the feature point of the ultrasound image.

Then, a small image is formed by collecting pixels around the feature point in the ultrasound image to acquire the patch image.

Since the sub-band HL frame image has a highlighted horizontal edge component and the sub-band LH frame image has a highlighted vertical edge component, the sub-band HL frame image and the sub-band LH frame image can sufficiently provide edge feature points that can be conveniently used for organ matching.

In addition, the overlapping pixel determination unit may also be used to select overlapping pixels between a sub-band HL frame image, a sub-band LH frame image, and a sub-band HH frame image acquired by wavelet frame transform of the reference organ image as the feature point of the reference organ image (that is, the reference feature point), wherein the overlapping pixels may be pixels having a value greater than a feature point determination threshold, which are found by performing pixel-by-pixel multiplication between the sub-band HL frame image, the sub-band LH frame image, and the sub-band HH frame image, followed by application of the feature point determination threshold on a pixel-by-pixel basis.

That is, the overlapping pixels of the reference organ image obtained by the overlapping pixel determination unit are selected as the reference feature point and the overlapping pixels of the ultrasound image obtained by the overlapping pixel determination unit are used as the matching feature point.

Then, the feature point of the reference organ image is compared with the feature point of each patch image to select patch images having a feature point with high similarity to the reference feature point, thereby generating a pair of feature points between the two images (the reference organ image and each of the selected patch images). Then, a correspondence between the feature points in the two images is ascertained to determine a geometric transformation relation between the two images. Then, the patch image is aligned with the reference organ image by geometric transformation based on the determined geometric transformation relation, followed by calculating a cross-correlation coefficient between the two images (the reference organ image and the geometrically transformed patch image). If the cross-correlation coefficient between the two images is greater than a predetermined threshold, it is determined that a corresponding organ is located in a current patch image in the ultrasound image.

In accordance with yet another aspect of the present invention, a remote medical diagnosis method using the apparatus for AI-based automatic ultrasound diagnosis of liver steatosis according to the present invention includes the steps of: extracting images of one or more regions of interest helpful to diagnosis of liver steatosis from an ultrasound image of a patient; concatenating and combining the images of the one or more regions of interest into one integrated image; transforming the integrated image into a shape-based integrated image or a pattern image; training the artificial neural network on the shape-based integrated image or the pattern image by deep learning; automatically determining, by a virtual doctor, a grade of liver steatosis based on the ultrasound image of the patient; and providing, by a remote medical diagnosis system, a remote consultation service with a medical expert.

It should be understood that the aforementioned solutions are provided for illustration only and are not to be construed in any way as limiting the present invention. In addition to the exemplary embodiments described above, other embodiments may exist in the drawings and detailed description of the invention.

As described above, in the field of ultrasound image processing, the present invention provides an apparatus for AI-based automatic ultrasound diagnosis of liver steatosis that can automatically determine the grade of liver steatosis, which is difficult to determine visually, through extraction from an image acquired by imaging medical examination using a deep learning trained artificial neural network, and a remote medical diagnosis method using the same.

However, it should be understood that the effects obtainable by the present invention are not limited to the aforementioned effects and other effects may exist.

DETAILED DESCRIPTION

Figure 1:
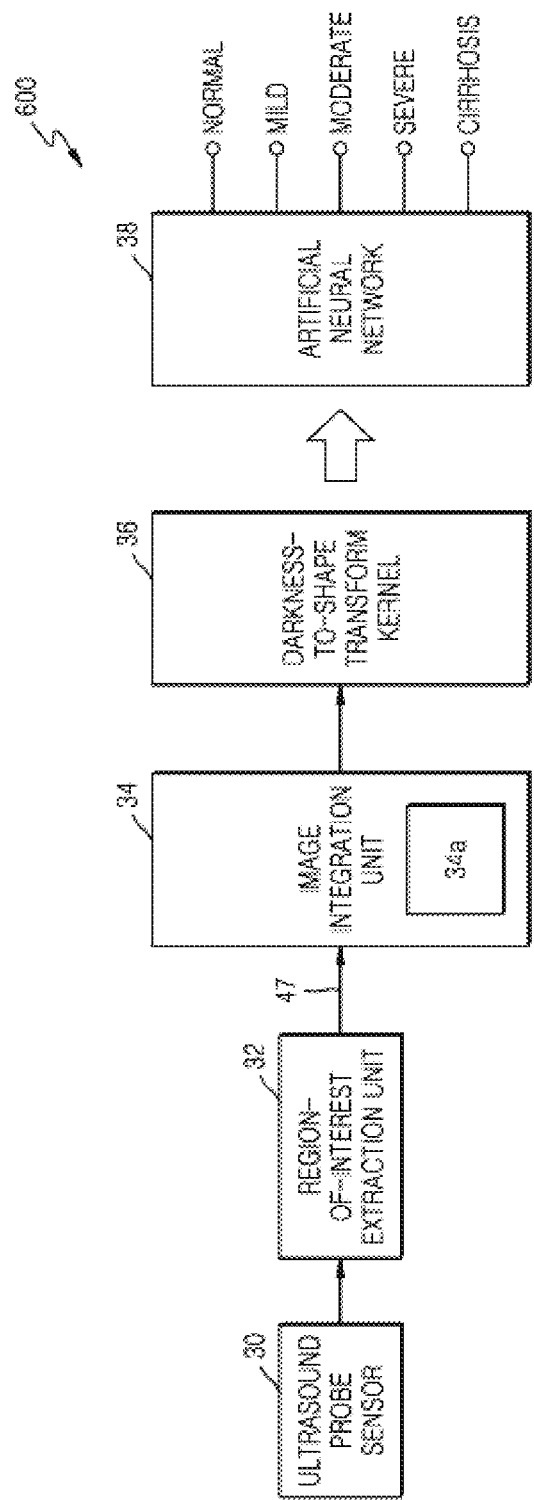
FIG. 1 is a block diagram of an apparatus for AI-based automatic ultrasound diagnosis of liver steatosis according to one embodiment of the present invention.

Now, exemplary embodiments of the present invention will be described in detail with reference to the accompanying drawings so that those skilled in the art can easily implement the present invention. It should be understood that the present invention is not limited to the following embodiments and may be embodied in different ways. In the drawings, portions irrelevant to the description will be omitted for clarity. Like components will be denoted by like reference numerals throughout the specification.

It will be understood that when an element is referred to as being "connected to" another element, it can be directly connected to the other element, or can be electrically or indirectly connected to the other element with a different element interposed therebetween.

It will be understood that when an element is referred to as being "on," "above," "at an upper end of," "under," "below," "at a lower end of" another element, it may directly adjoin the other element or layer, or intervening elements may be present.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups.

Hereinafter, exemplary embodiments of the present invention will be described in detail with reference to the accompanying drawings.

FIG. 1 is a block diagram of an apparatus for AI-based automatic ultrasound diagnosis of liver steatosis 600 according to one embodiment of the present invention. The apparatus for AI-based automatic ultrasound diagnosis of liver steatosis according to this embodiment includes: an ultrasound probe sensor 30 acquiring an ultrasound image from a patient; a region-of-interest extraction unit 32 extracting images of one or more regions of interest from the ultrasound image; an image integration unit 34 concatenating the images of the one or more regions of interest into one integrated image; a darkness-to-shape transform kernel 36 transforming the integrated image into a shape-based integrated image; and an artificial neural network 38 trained on the shape-based integrated image by deep learning, wherein the deep learning-trained artificial neural network 38 automatically determines a grade of liver steatosis in the patient as normal, mild, moderate, severe, or cirrhosis based on the ultrasound image of the patient received from the ultrasound probe sensor 30.

Referring to FIG. 1, in another embodiment, the image integration unit 34 may further include a rearrangement unit 34a to acquire a pattern image of each of the images of the regions of interest. The image integration unit 34 may concatenate the pattern images into one integrated image and the artificial neural network 38 may be directly trained on the integrated image by deep learning. In this case, the darkness-to-shape transform kernel 36 may be omitted.

FIG. 2 is a block diagram of an apparatus for AI-based automatic ultrasound diagnosis of liver steatosis 600 according to another embodiment of the present invention. The apparatus for AI-based automatic ultrasound diagnosis of liver steatosis according to this embodiment includes: an ultrasound probe sensor 30 acquiring an ultrasound image from a patient; a region-of-interest extraction unit 32 extracting images of one or more regions of interest from the ultrasound image; an image integration unit 34 concatenating the images of the one or more regions of interest into one integrated image; a wavelet transform unit 35 decomposing the integrated image into sub-band images by discrete wavelet transform; and an artificial neural network trained on the sub-band images by deep learning, wherein the deep learning trained artificial neural network automatically determines a grade of liver steatosis in the patient based on the ultrasound image of the patient received from the ultrasound probe sensor 30.

Referring to FIG. 2, the apparatus for AI-based automatic ultrasound diagnosis of liver steatosis according to this embodiment may further include a darkness-to-shape transform kernel 36 disposed in-line between the wavelet transform unit 35 and the artificial neural network 38 to transform the sub-band images into a shape-based sub-band image, wherein the artificial neural network 38 may be trained on the shape-based sub-band images by deep learning.

Figure 2A:
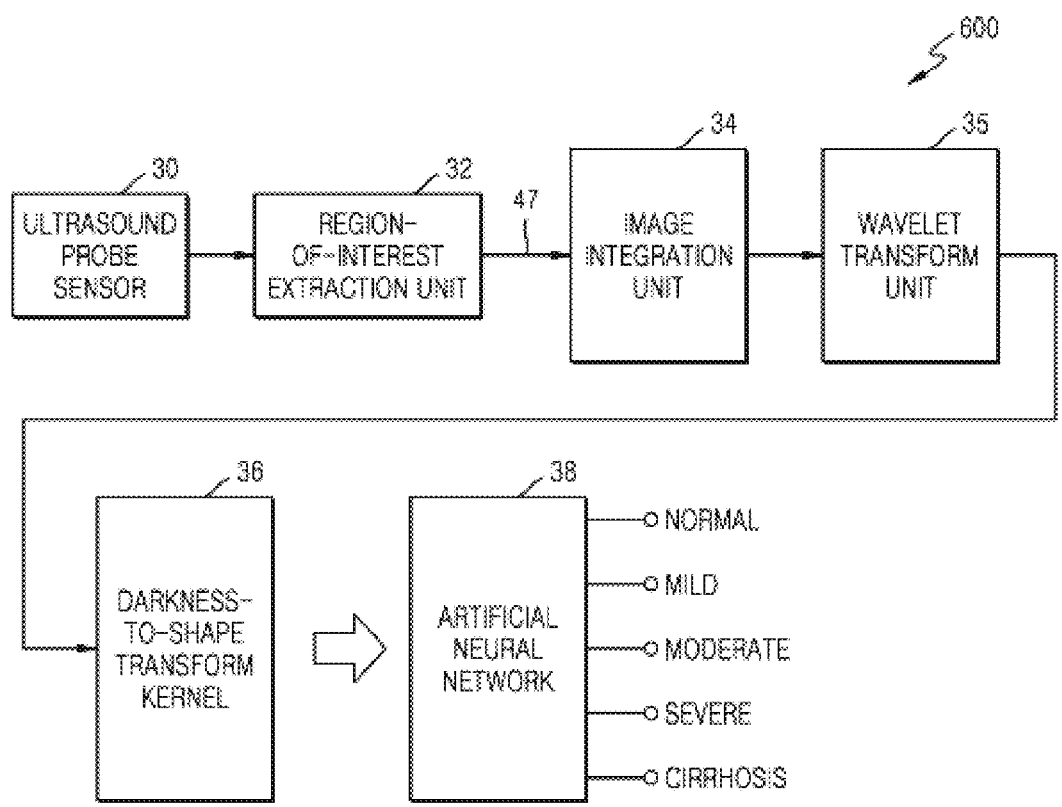
FIGS. 2A and 2B are a block diagram of an apparatus for AI-based automatic ultrasound diagnosis of liver steatosis according to another embodiment of the present invention embodiment, wherein a darkness-to-shape transform kernel transforming sub-band images into a shape-based sub-band image is further disposed in-line between a wavelet transform unit and an artificial neural network to train the artificial neural network on the shape-based sub-band images by deep leaning.
Figure 2B:
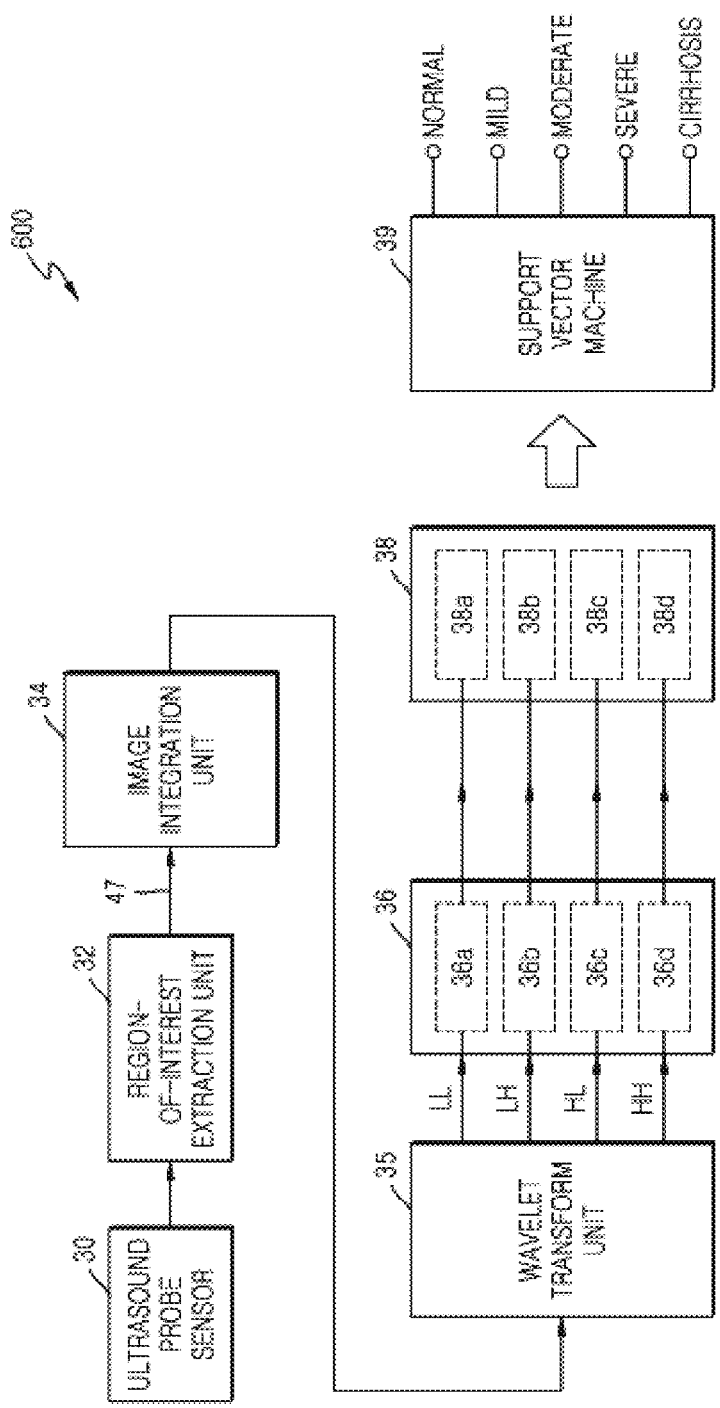

Specifically, FIG. 2(a) shows an embodiment in which a darkness-to-shape transform kernel 36 transforming the sub-band images into one shape-based sub-band image is disposed in-line between the wavelet transform unit 35 and the artificial neural network 38, such that one artificial neural network 38 is trained on the one shape-based sub-band image by deep learning, and FIG. 2(b) shows an embodiment in which a darkness-to-shape transform kernel 36 transforming the sub-band images into respective shape-based sub-band images is disposed in-line between the wavelet transform unit 35 and the artificial neural network 36, such that plural independent artificial neural networks 38 are trained on the respective shape-based sub-band images by deep learning.

In addition, referring to FIG. 2(b), a support vector machine 39 performing machine learning may be further disposed downstream of the artificial neural networks 38 to collect results of analysis by the independent artificial neural networks 38 to determine the grade of liver steatosis, wherein the support vector machine 39 conducts classification of liver steatosis based on feature vectors received from the artificial neural networks 38.

The darkness-to-shape transform kernel 36 shown in FIG. 2(b) is adapted to transform each of the sub-band images generated by the wavelet transform unit 35 into a shape-based sub-band image, and may include a first kernel 36a transforming a sub-band LL image into a shape-based sub-band LL image; a second kernel 36b transforming a sub-band LH image into a shape-based sub-band LH image; a third kernel 36c transforming a sub-band HL image into a shape-based sub-band HL image; and a fourth kernel 36d transforming the sub-band HH image into a shape-based sub-band HH image.

The artificial neural network 38 shown in FIG. 2(b) may include: a first artificial neural network 38a trained on the shape-based sub-band LL image; a second artificial neural network 38b trained on the shape-based sub-band LH image; a third artificial neural network 38c trained on the shape-based sub-band HL image; and a fourth artificial neural network 38d trained on the shape-based sub-band HH image.

Figure 3:
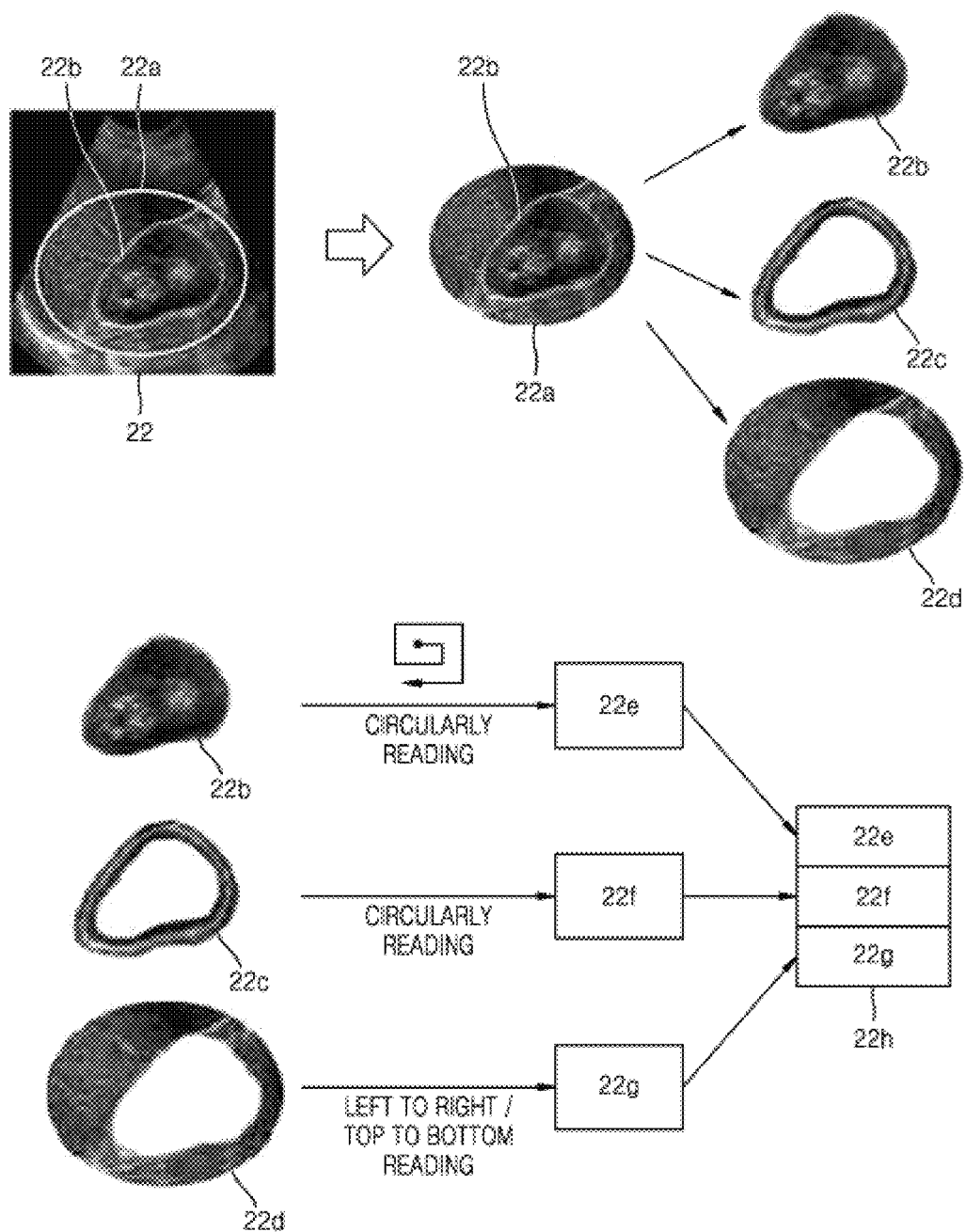
FIG. 3 is a diagram illustrating a process of acquiring a pattern image and an integrated image by an image integration unit.

FIG. 3 is a diagram illustrating a process of acquiring a pattern image and an integrated image by the image integration unit 34. First, the region-of-interest extraction unit 32 acquires a first image 22a by extracting a region including a kidney and a liver from an ultrasound image 22 in a parasagittal scan plane using an elliptical window, acquires a second image 22b by extracting only a kidney region from the first image 22a, acquires a kidney border image 22c by extraction along a boundary between the first image 22a and the second image 22b, and acquires a third image 22d by extracting the remaining portion of the first image 22a excluding the second image 22b and the kidney border image 22c.

Then, the image integration unit 34 generates a pattern image 22e of the second image 22b by sequentially reading image pixels in the second image 22b while circularly moving starting from center coordinates of the second image 22b to form a rectangular image 22e. In addition, the image integration unit 34 generates a pattern image 22f of the kidney border image 22c by sequentially reading image pixels in the kidney border image 22c while circularly moving along the kidney border image 22c to form a rectangular image 22f.

Further, the image integration unit 34 generates a pattern image 22g of the third image 22d by sequentially reading image pixels in the third image 22d while scanning the third image from left to right and top to bottom to form a rectangular image. Then, the image integration unit 34 combines the generated pattern images 22e, 22f, 22g into an integrated image 22h.

An image pattern in the integrated image 22h significantly differs between different liver steatosis grades and thus can be efficiently learned and recognized by the artificial neural network.

Figure 4:
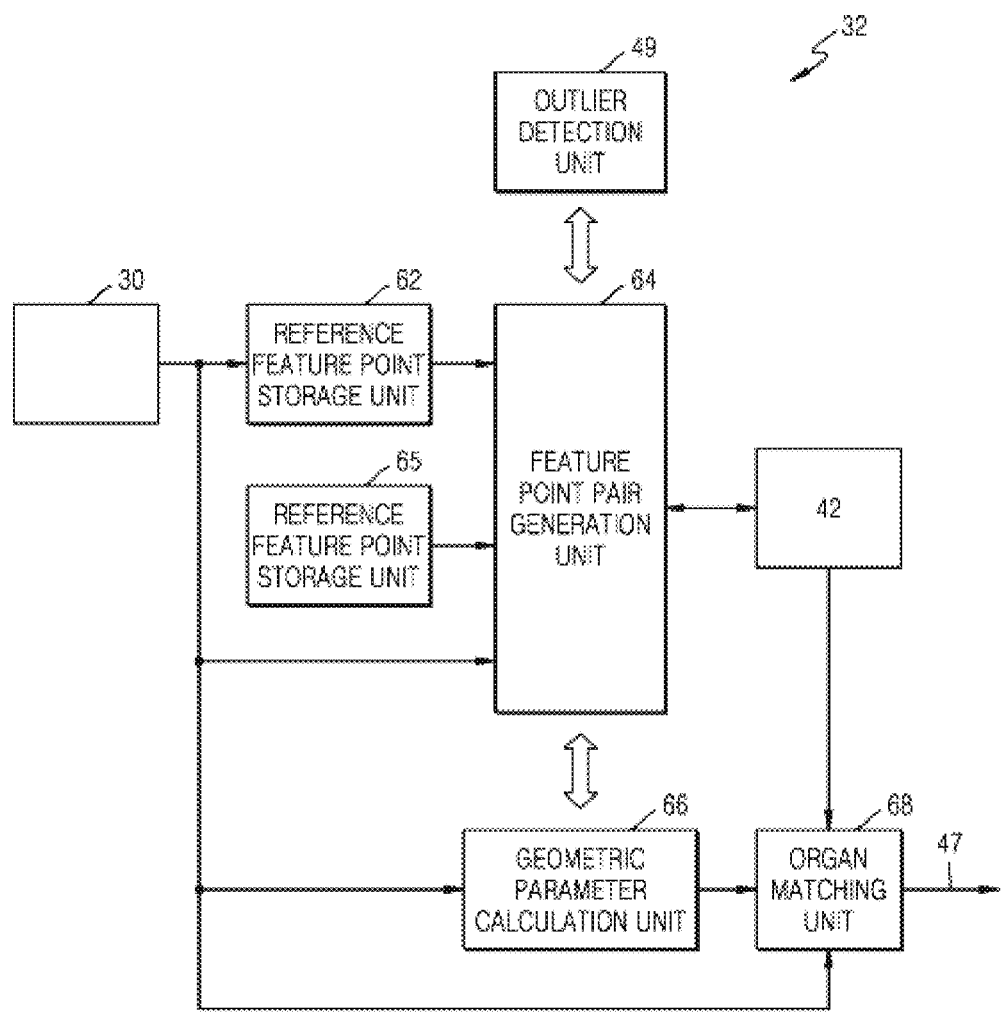
FIG. 4 is a block diagram of a region-of-interest extraction unit extracting a region of interest from an ultrasound image acquired by an ultrasound probe sensor according to one embodiment of the present invention.

FIG. 4 is a block diagram of the region-of-interest extraction unit 32 extracting a region of interest from an ultrasound image acquired by the ultrasound probe sensor 30 according to one embodiment of the present invention. The region-of-interest extraction unit 32 according to this embodiment includes: an organ image database 42 storing reference organ images as a reference for organ matching; a reference feature point storage unit 65 storing a feature point of each of the reference organ images; a feature point detection unit 62 extracting matching feature points from the ultrasound image; a feature point pair generation unit 64 comparing the reference feature point with the matching feature point of each patch image, which is formed around the matching feature point, to select patch images having a matching feature point with high similarity to the reference feature point and generating a pair of feature points between the reference organ image and each of the selected patch images; an outlier detection unit 49 eliminating abnormal pairs of feature points among the generated pairs of feature points; a geometric parameter calculation unit 66 calculating geometric parameters required for registration between the resultant pair of feature points, the geometric parameters including translation, rotation and scaling; and an organ matching unit 68 acquiring a registered patch image using the geometric parameters, calculating a cross-correlation coefficient between the registered patch image and the reference organ image, determining that a corresponding organ is located in a current patch image in the ultrasound image if the cross-correlation coefficient is greater than a predetermined threshold, extracting an organ image region at a corresponding location, and transmitting the organ image region to the image integration unit 34.

The organ image region may include at least one selected from the group of the first image, the second image obtained by extracting only a kidney region from the first image, the kidney border image obtained by extraction along the boundary between the first image and the second image, and the third image obtained by extracting the remaining region of the first image excluding the second image and the kidney border image.

Figure 5:
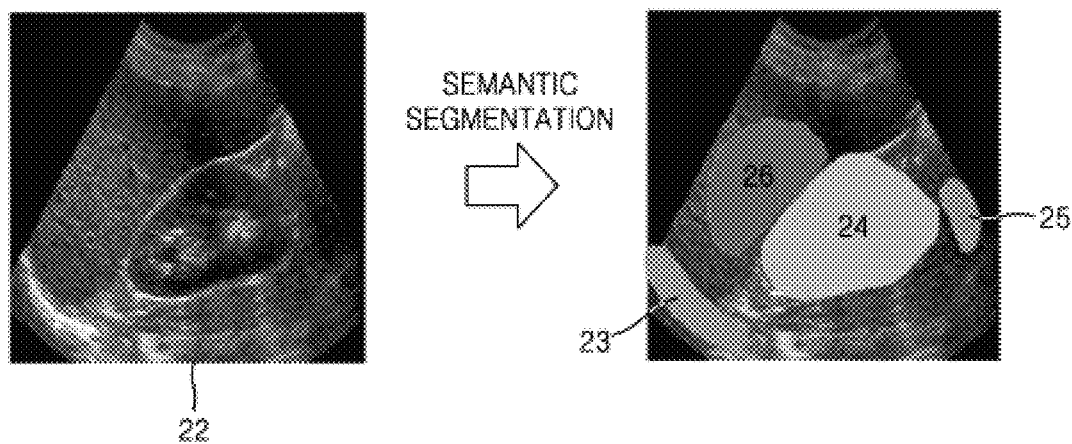
FIG. 5 shows an exemplary ultrasound image in which different organs are labeled with different colors, the ultrasound image being obtained by semantic segmentation of an ultrasound image in a parasagittal scan plane.

FIG. 5 shows an exemplary ultrasound image in which different organs are labeled with different colors, the ultrasound image being obtained by semantic segmentation of an ultrasound image 22 in a parasagittal scan plane.

In FIG. 5, reference numeral 26 denotes a liver, reference numeral 25 denotes a spleen, reference numeral 24 denotes a kidney, and reference numeral 23 denotes a diaphragm.

Figure 6:
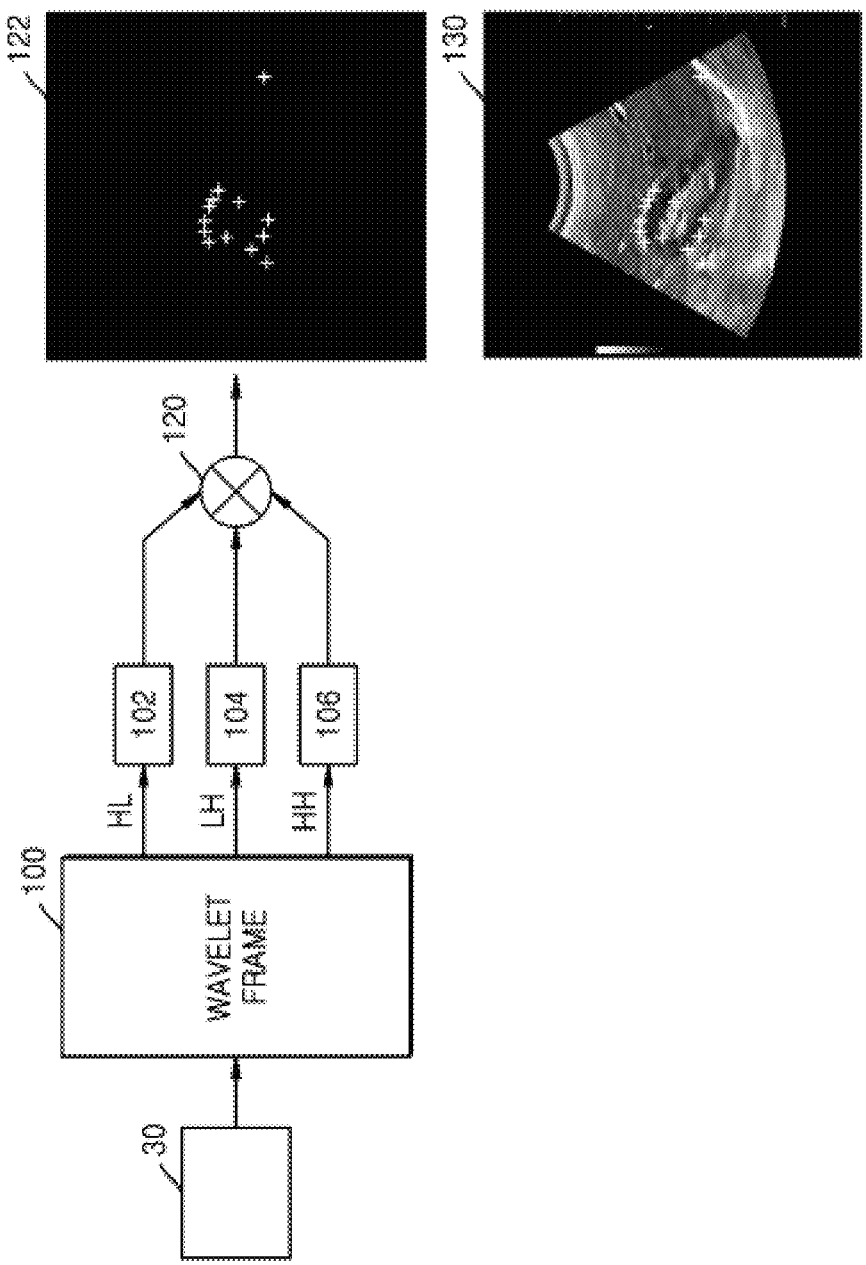
FIG. 6 is a diagram of a feature point detection unit selecting overlapping pixels between sub-band frame images as a feature point according to one embodiment of the present invention.

FIG. 6 is a diagram of the feature point detection unit 62 selecting overlapping pixels between sub-band frame images as a feature point according to one embodiment of the present invention. The feature point detection unit 62 includes: an ultrasound probe sensor 30 acquiring an ultrasound image from an examination area of a patient; a wavelet frame unit 100 acquiring a sub-band HL frame image, a sub-band LH frame image, and a sub-band HH frame image by wavelet frame transform of the ultrasound image; feature point determination units 102, 104, 106 applying a feature point determination threshold to the respective sub-band frame images on a pixel-by-pixel basis; and an overlapping pixel determination unit 120 detecting overlapping pixels by multiplication between the sub-band frame images with respect to pixels having a value greater than the feature point determination threshold. In FIG. 6, corner points (indicated by '+' in the drawing) can be found in a resultant image 122 from the overlapping pixel determination unit 120.

Reference numeral 130 denotes an exemplary ultrasound image having the corner points superimposed thereon. The feature point pair generation unit 64 generates pairs of feature points composed of the corner points (indicated by '+') and corresponding feature points stored in the reference feature point storage unit 65, and the geometric parameter calculation unit 66 calculates geometric parameters required for registration between the generated pair of feature points, wherein the geometric parameters may include translation, rotation, and scaling.

Figure 7:
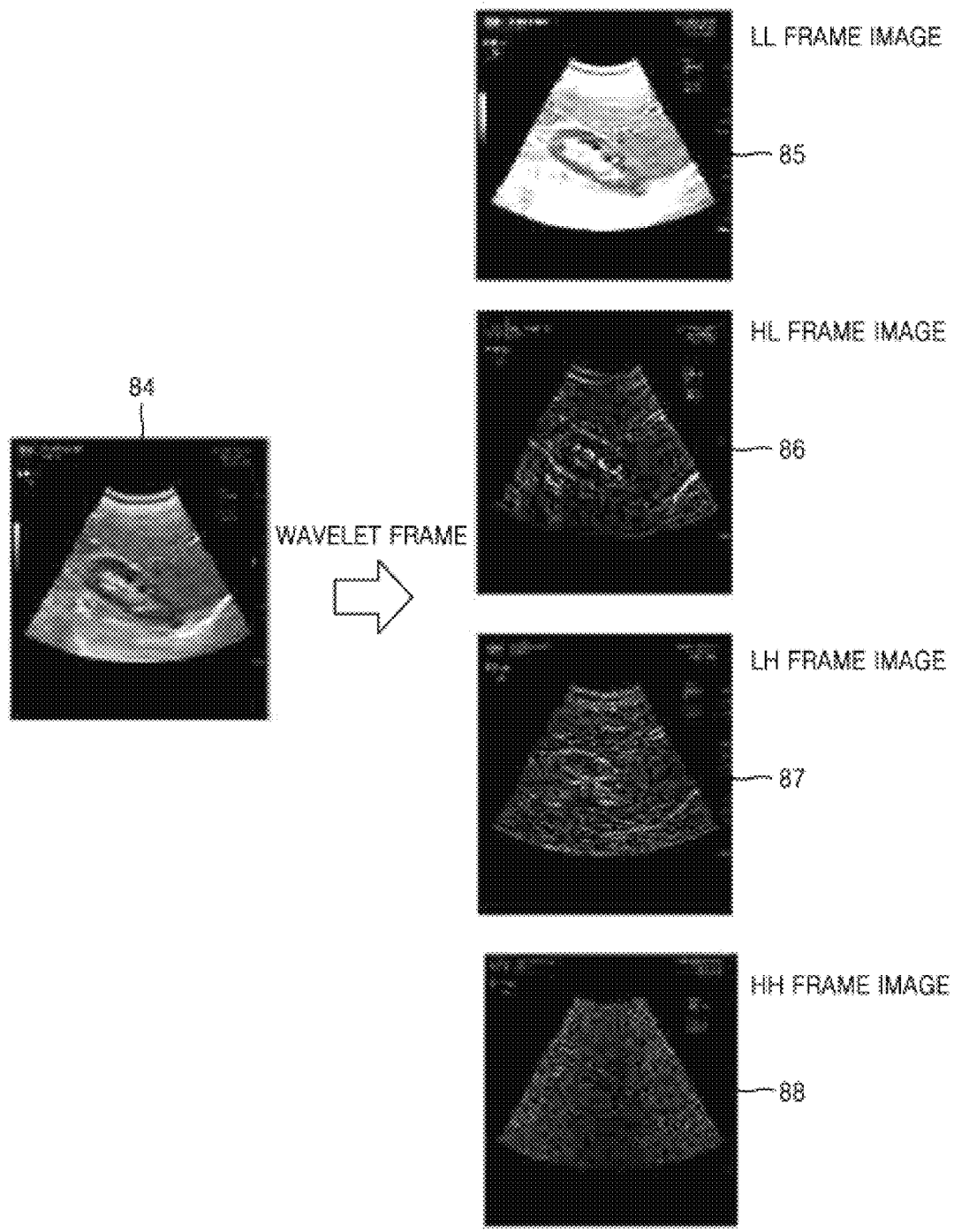
FIG. 7 shows exemplary sub-band frame images obtained by applying wavelet frame transformation to an ultrasound image.

FIG. 7 shows a sub-band LL frame image 85, a sub-band HL frame image 86, a sub-band LH frame image 87, and a sub-band HH frame image 88 acquired by applying wavelet frame transform to an ultrasound image 84.

Since wavelet frame transform does not include a sub-sampling process, image size does not change before and after transform.

Figure 8:
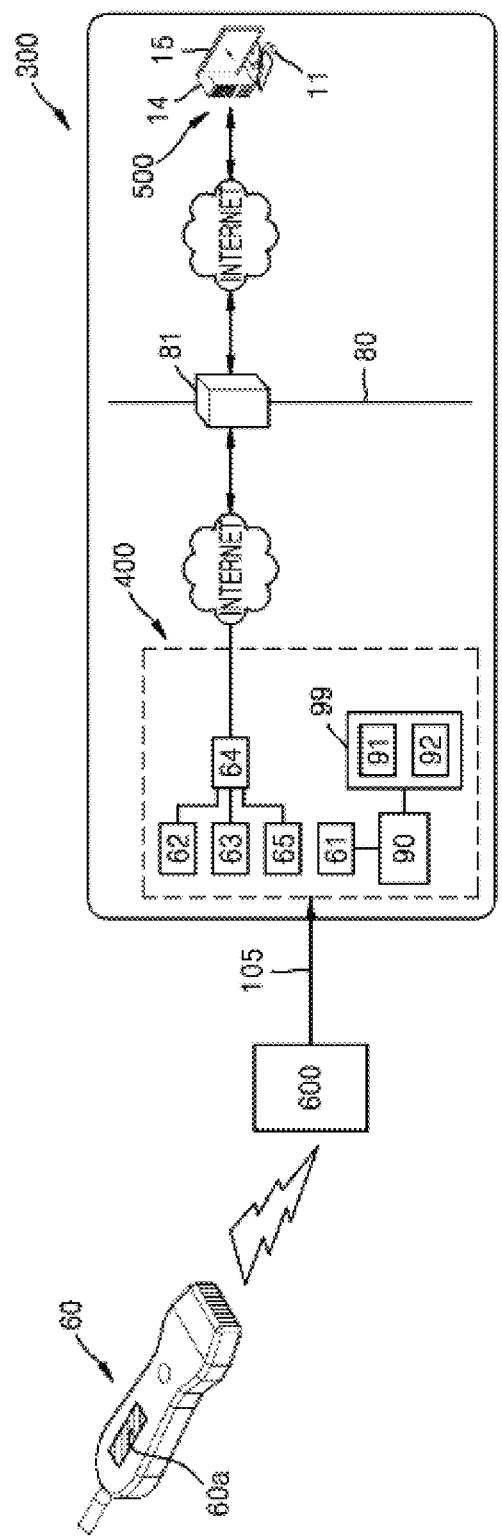
FIG. 8 is a diagram of an apparatus for AI-based automatic ultrasound diagnosis of liver steatosis provided with a remote diagnosis system according to one embodiment of the present invention.

FIG. 8 is a diagram of an apparatus for AI-based automatic ultrasound diagnosis of liver steatosis according to a further embodiment of the present invention, wherein an ultrasound medical device 60 is connected to a remote medical diagnosis system 300 such that an AI-based virtual doctor 99 residing in the remote medical diagnosis system automatically analyzes medical image data of a patient to perform diagnosis. The remote medical diagnosis system 300 may include: an ultrasound medical device 60 provided with an ultrasound probe sensor 30; a wireless transmitter 60*a* integrated in the ultrasound medical device 60 to wirelessly transmit medical image data of a patient measured by the ultrasound medical device 60; the apparatus for AI-based automatic ultrasound diagnosis of liver steatosis 600 according to the present invention, the apparatus receiving an ultrasound image of the patient from the wireless transmitter 60*a* and automatically determining a grade of liver steatosis; a user terminal 400 including a camera 61 monitoring use of the ultrasound medical device 60, a first authentication unit 93 wirelessly authenticating product ID of the ultrasound medical device 60, a recording unit 94 storing the ultrasound image of the patient obtained by the ultrasound medical device 60, an Internet connector 96 transmitting the ultrasound image and the product ID of the ultrasound medical device 60 to a remote diagnosis server 81 via a communication network 80 and providing a communication channel for a remote consultation service, and a first consultation service unit providing a consultation service with a medical expert; a communication interface 105 providing a connection to the apparatus for AI-based automatic ultrasound diagnosis of liver steatosis 600 and the user terminal 400; an artificial neural network 90 residing as software in the user terminal 400 and trained on a medical image database accumulated by the ultrasound medical device 60 by deep learning; a virtual doctor 99 residing as software in the user terminal 400 and including a guide unit 91 guiding or instructing how to use the ultrasound medical device 60 and a diagnosis unit 92 outputting a diagnostic result obtained by automatic analysis of the medical image data of the patient obtained by the ultrasound medical device 60 using the deep learning-trained artificial neural network 90; and a medical expert terminal 200 including a receiver (not shown) receiving the medical image data and the ultrasound image via the communication network 80 and a second consultation service unit providing a consultation service between a user and a medical expert.

The guide unit 91 serves to guide or instruct a user on how to use the ultrasound medical device 60 based on results of monitoring use of the ultrasound medical device 60 in real time using the camera 61.

The medical expert terminal 200 may further include a camera 14, a microphone 15, and a mouse 11.

Next, based on the details described above, an apparatus for AI-based automatic ultrasound diagnosis of liver steatosis according to various embodiments of the present invention will be briefly discussed.

An apparatus for AI-based automatic ultrasound diagnosis of liver steatosis 600 according to one embodiment of the present invention may include a probe sensor 30, a region-of-interest extraction unit 32, an image integration unit 34, a darkness-to-shape transform kernel 36, and an artificial neural network 38.

The ultrasound probe sensor 30 may acquire an ultrasound image from a patient.

The region-of-interest extraction unit 32 may acquire images of one or more regions helpful to diagnosis of liver steatosis from the ultrasound image. The images of the regions of interest may be used in diagnosis of liver steatosis. The region-of-interest extraction unit 32 may extract the images of the regions of interest from the ultrasound image acquired by the ultrasound probe sensor 30. The images extracted or generated by the region-of-interest extraction unit 32 to be transmitted to the image integration unit 34 are designated by reference numeral 47 in FIG. 1 to FIG. 4.

The image integration unit 34 may combine the images of the one or more regions of interest into one integrated image. For example, if there is only an image of one region of interest, the image itself may be used as the integrated image. If there are images of plural regions of interest, the images may be combined into one integrated image.

The darkness-to-shape transform kernel 36 may transform the integrated image into a shape-based integrated image.

The artificial neural network 38 may be trained in advance on the shape-based integrated image by deep learning. In addition, the artificial neural network 38 trained in advance on the shape-based integrated image by deep learning may automatically determine a grade of liver steatosis based on the ultrasound image of the patient received from the ultrasound probe sensor 30.

In addition, an apparatus for AI-based automatic ultrasound diagnosis of liver steatosis 600 according to another embodiment of the present invention may include an ultrasound probe sensor 30, a region-of-interest extraction unit 32, an image integration unit 34, and an artificial neural network 38, wherein a darkness-to-shape transform kernel 36 may be omitted.

The image integration unit 34 may include a rearrangement unit 34*a*. The rearrangement unit 34*a* rearranges the images of the one or more regions of interest acquired by the region-of-interest extraction unit 32 to acquire pattern images. The image integration unit 34 may combine the pattern images into one integrated image.

If there are images of plural regions of interest, the rearrangement unit 34*a* may rearrange the images into respective pattern images.

For example, the rearrangement unit 34*a* may receive a first image 22*a*, a second image 22*b*, a kidney border image 22*c*, and a third image 22*d* from the region-of-interest extraction unit 32, the first image being obtained by extracting a region including a liver and a kidney from the ultrasound image, the second image being obtained by extracting only a kidney region from the first image, the kidney border image being obtained by extraction along a boundary between the first image and the second image, and the third image being 22*d* being obtained by extracting the remaining portion of the first image excluding the second image and the kidney border image. Then, the rearrangement unit 34*a* may generate a pattern image 22*e* of the second image 22*b* by taking image pixels from the second image 22*b* while circularly moving starting from center coordinates of the second image 22*b* and rearranging the taken image pixels into a rectangular image, generate a pattern image 22*f* of the kidney border image 22*c* by taking image pixels from the kidney border image 22*c* while circularly moving along the kidney border image 22*c* and rearranging the taken image pixels into a rectangular image, and generate a pattern image 22*g* of the third image 22*d* by taking image pixels from the third image 22*d* by pixel scanning and rearranging the taken image pixels into a rectangular image.

Here, a region extracted from the ultrasound image by the region-of-interest extraction unit 32 may be selected from among regions of the organs of interest described above, including a liver region and a kidney region.

As used herein, the expression "taking image pixels from the second image, the kidney border image, and the third image" may mean that the rearrangement unit 34*a* reads or scans the image pixels. In addition, the expression "taking image pixels from the third image by pixel scanning" may mean scanning the image pixels according to a predetermined pixel scanning scheme, as described above.

It should be understood that the image pixels taken by the rearrangement unit 34*a* may be rearranged into images having various shapes such as a circular shape, without being limited to a rectangular image.

In addition, an apparatus for AI-based automatic ultrasound diagnosis of liver steatosis 600 according to a further embodiment of the present invention may include an ultrasound probe sensor 30, a region-of-interest extraction unit 32, an image integration unit 34, a wavelet transform unit 35, and an artificial neural network 38.

The wavelet transform unit 35 may decompose the integrated image generated by the image integration unit 34 into sub-band images by discrete wavelet transform. Here, the sub-band images include a sub-band LL image, a sub-band LH image, a sub-band HL image, and a sub-band HH image.

The artificial neural network 38 may be trained in advance on the sub-band images generated by the wavelet transform unit 35 by deep learning. In addition, the artificial neural network 38 trained in advance on the sub-band images by deep learning may automatically determine a grade of liver steatosis based on an ultrasound image of a patient received from the ultrasound probe sensor 30. Wavelet transform can improve effectiveness in learning and accuracy of determination.

In addition, the apparatus for AI-based automatic ultrasound diagnosis of liver steatosis 600 according to this embodiment may further include a darkness-to-shape transform kernel 36.

Here, the darkness-to-shape transform kernel 36 may transform the sub-band images into a shape-based sub-band image. In addition, the artificial neural network 38 may be trained in advance on the shape-based sub-band image by deep learning. The deep learning-trained artificial neural network 38 may automatically determine a grade of liver steatosis in a patient based on the shape-based sub-band image.

The region-of-interest extraction unit 32 according to the present invention may extract images of at least two selected from the group of liver, right portal vein (RPV), hepatic vein, kidney, spleen, and diaphragm regions from an ultrasound image. Here, the liver, the hepatic vein, the kidney, the spleen, and the diaphragm may be included in the organ of interest described above and may be replaced with other organs that can be used in diagnosis of liver steatosis.

In addition, the region-of-interest extraction unit 32 according to one embodiment of the present invention may include an organ image database 42, a reference feature point storage unit 65, a feature point detection unit 62, a feature point pair generation unit 64, an outlier detection unit 49, a geometric parameter calculation unit 66, and an organ matching unit 68.

The organ image database 42 may store reference organ images as a reference for organ matching.

The reference feature point storage unit 65 may store feature points of the reference organ images.

The feature point detection unit 62 may extract matching feature points from the ultrasound image.

The feature point pair generation unit 64 may compare the reference feature point with the matching feature point of each patch image, which is formed around the matching feature point, to select patch images having a matching feature point with high similarity to the reference feature point to generate a pair of feature points between the reference organ image and each of the selected patch images. Here, the similarity to the reference feature point may be determined, for example, by creating a vector between the reference feature point and the matching feature point, calculating the length of the vector, and comparing the calculated vector length with a predetermined value.

The outlier detection unit 49 may eliminate abnormal pairs of feature points among the generated pairs of feature points. For example, when the length of a vector between a pair of feature points exceeds a predetermined outlier threshold, the pair of feature points may be eliminated.

The geometric parameter calculation unit 66 may calculate geometric parameters required for registration between the pair of feature points obtained by the feature point pair generation unit 64, wherein the geometric parameters may include translation, rotation, and scaling.

The organ matching unit 68 may acquire a registered patch image using the geometric parameters calculated by the geometric parameter calculation unit 66, calculate a cross-correlation coefficient between the registered patch image and the reference organ image, determine that a corresponding organ is located in a current patch image in the ultrasound image if the cross-correlation coefficient is greater than a predetermined threshold, extract an organ image region at a corresponding location, and transmit the organ image region to the image integration unit. In FIG. 4, reference numeral 47 may denote the organ image region transmitted to the image integration unit 34 from the organ matching unit 68.

In another embodiment, the region-of-interest extraction unit 32 may include an artificial neural network performing semantic segmentation on the ultrasound image to acquire a semantic segmented ultrasound image in which different organs of interest are labeled with different values or different colors for extraction of the images of the regions of interest. The region-of-interest extraction unit 32 may generate a first image by extracting a region including a kidney and a liver from the ultrasound image by semantic segmentation, generate a second image by extracting only a kidney region from the first image by semantic segmentation, generate a kidney border image by extraction along a boundary between the first image and the second image, generate a third image by extracting the remaining portion of the first image excluding the second image and the kidney border image, and transmit the second image, the kidney border image, and the third image to the image integration unit.

Here, the kidney and the liver may be replaced with other organs as described above.

In a further embodiment, the region-of-interest extraction unit 32 may include a wavelet frame unit 100, a feature point detection unit 62, a feature point pair generation unit 64, a geometric parameter calculation unit 66, and an organ matching unit 68. Here, the feature point detection unit 62 may include feature point determination units 102, 104, 106 and an overlapping pixel determination unit 120.

The wavelet frame unit 100 may perform wavelet frame transform on the reference organ image and the ultrasound image to acquire a sub-band HL frame image, a sub-band LH frame image, and a sub-band HH frame image.

The feature point determination units 102, 104, 106 may apply a feature point determination threshold to the respective sub-band frame images on a pixel-by-pixel basis.

The overlapping pixel determination unit 120 may find overlapping pixels by multiplication between the sub-band frame images with respect to pixels having a value greater than the feature point determination threshold.

The feature point detection unit 62 may select overlapping pixels of the reference organ image obtained by the overlapping pixel determination unit 120 as the reference feature point and select overlapping pixels of the ultrasound image obtained by the overlapping pixel determination unit 120 as the matching feature point.

An apparatus for AI-based automatic ultrasound diagnosis of liver steatosis according to a further embodiment of the present invention (hereinafter referred to as "apparatus for AI-based automatic ultrasound diagnosis of liver steatosis including a remote medical diagnosis system") may include a remote medical diagnosis system including an ultrasound medical device 60, the apparatus for AI-based automatic ultrasound diagnosis of liver steatosis 600 according to the above embodiments, a communication interface (not shown), a user terminal 400, and a medical expert terminal 200.

The ultrasound medical device 60 may include an ultrasound probe sensor 30 and a wireless transmitter 60a. The wireless transmitter 60a may be integrated in the ultrasound medical device 60 to wirelessly transmit medical image data of a patient measured by the ultrasound medical device 60.

The apparatus for AI-based automatic ultrasound diagnosis of liver steatosis 600 may receive an ultrasound image of the patient from the wireless transmitter 60a and automatically determine a grade of liver steatosis. The apparatus for AI-based automatic ultrasound diagnosis of liver steatosis including the remote medical diagnosis system may include the apparatus for AI-based automatic ultrasound diagnosis of liver steatosis 600 according to the above embodiments of the present invention.

The communication interface (not shown) may provide a connection to the apparatus for AI-based automatic ultrasound diagnosis of liver steatosis 600 and the user terminal 400. For example, data such as the integrated image, the pattern image, and the liver steatosis grade of the patient may be transmitted to the user terminal 400 from the apparatus for AI-based automatic ultrasound diagnosis of liver steatosis 600 via the communication interface.

The user terminal 400 may include a camera 61, a first authentication unit 93, a recording unit 94, an internet connector 96, and a first consultation service unit 95. Here, the camera 61 may monitor use of the ultrasound medical device 60. The first authentication unit 93 may wirelessly authenticate a product ID of the ultrasound medical device 60. The recording unit 94 may store the ultrasound image of the patient acquired by the ultrasound medical device 60. In addition, the recording unit 94 may store the data transmitted to the user terminal 400 from the apparatus for AI-based automatic ultrasound diagnosis of liver steatosis 600. The internet connector 64 may transmit the ultrasound image and the product ID of the ultrasound medical device 60 to a remote diagnosis server 81 via a communication network 80 and may provide a communication channel for a remote consultation service. The first consultation service unit 95 may provide a consultation service with a medical expert.

In addition, the user terminal 400 may further include an artificial neural network 90 and a virtual doctor 99 including a guide unit 91 and a diagnosis unit 92. Here, the artificial neural network 90 and the virtual doctor 99 may reside as software in the user terminal 400.

The artificial neural network 90 may be trained on a medical image database accumulated by the ultrasound medical device 60 by deep learning.

The guide unit 91 may guide or instruct how to use the ultrasound medical device 60 and the diagnosis unit 92 may output a diagnostic result obtained by automatic analysis of the medical image data of the patient acquired by the ultrasound medical device 60 using the deep learning-trained artificial neural network 90.

The medical expert terminal 200 may include a receiver (not shown) and a second consultation service unit (not shown).

The receiver (not shown) may receive the medical image data or the ultrasound image via the communication network 80 and the second consultation service unit (not shown) may provide a consultation service between a user and a medical expert.

A remote medical diagnosis method according to one embodiment of the present invention may include the steps of: extracting images of one or more regions of interest helpful to diagnosis of liver steatosis from an ultrasound image of a patient; generating one integrated image by concatenating and combining the images of the one or more regions of interest into one; transforming the integrated image into a shape-based integrated image or a pattern image; training an artificial neural network on the shape-based integrated image or the pattern image by deep learning; automatically determining, by a virtual doctor, a grade of liver steatosis based on the ultrasound image of the patient; and providing, by a remote medical diagnosis system, a remote consultation service with a medical expert.

The remote medical diagnosis method according to the present invention may be carried out based on the various embodiments of the apparatus for AI-based automatic ultrasound diagnosis of liver steatosis and the remote medical diagnosis system set forth above.

The remote medical diagnosis method according to the present invention may be realized in the form of program instructions which can be implemented through various computer components, and may be recorded in a computer-readable storage medium. The computer-readable storage medium may include program instructions, a data file, a data structure, and the like either alone or in combination thereof. The program instructions recorded in the computer-readable storage medium may be any program instructions particularly designed and structured for the present invention or known to those skilled in the field of computer software. Examples of the computer-readable storage medium include magnetic recording media, such as hard disks, floppy disks and magnetic tapes, optical data storage media, such as CD-ROMs and DVD-ROMs, magneto-optical media such as floptical disks, and hardware devices, such as read-only memories (ROMs), random-access memories (RAMs), and flash memories, which are particularly structured to store and implement the program instructions. Examples of the program instructions include not only assembly language code formatted by a compiler but also high-level language code which can be implemented by a computer using an interpreter. The hardware device described above may be configured to operate as one or more software modules to perform operations of the present invention, and vice versa.

In addition, the remote medical diagnosis method may be implemented in the form of a computer-executable computer program or application stored in a recording medium.

Although some embodiments have been described herein, it should be understood that these embodiments are provided for illustration and that various modifications, changes, alterations, and equivalent embodiments can be made by those skilled in the art without departing from the spirit and scope of the invention. Therefore, the embodiments are not to be construed in any way as limiting the present invention. For example, each component described as a single type may be implemented in a distributed manner, and, similarly, components described as distributed may be implemented in a combined form.

The scope of the present application should be defined by the appended claims and equivalents thereof rather than by the detailed description, and all changes or modifications derived from the spirit and scope of the claims and equivalents thereof should be construed as within the scope of the present invention.

LIST OF REFERENCE NUMERALS

600: Apparatus for AI-based automatic ultrasound diagnosis of liver steatosis
30: Ultrasound probe sensor
32: Region-of-interest extraction unit
34: Image integration unit
34a: Rearrangement unit
36: Darkness-to-shape transform kernel
38: Artificial neural network
35: Wavelet transform unit

What is claimed is:

1. An apparatus for AI-based automatic ultrasound diagnosis of liver steatosis, the apparatus comprising:
an ultrasound probe sensor configured to acquire an ultrasound image from a patient;
a region-of-interest extraction unit configured to acquire images of one or more regions of interest helpful to diagnosis of liver steatosis from the ultrasound image;
an image integration unit comprising a rearrangement unit configured to rearrange the images of the one or more regions of interest acquired by the region-of-interest extraction unit to acquire a pattern image, the image integration unit configured to combine the rearranged images into one integrated image; and
an artificial neural network trained on the integrated image by deep learning,
wherein the deep learning-trained artificial neural network is configured to automatically determine a grade of liver steatosis in the patient based on the ultrasound image of the patient received from the ultrasound probe sensor,
wherein the rearrangement unit is configured to receive a first image, a second image, a kidney border image, and a third image from the region-of-interest extraction unit, the first image includes a kidney region and a liver region from the ultrasound image, the second image includes only the kidney region from the first image, the kidney border image includes a boundary between the first image and the second image, and the third image includes the remaining portion of the first image excluding the second image and the kidney border image; the rearrangement unit is configured to take image pixels from the second image while circularly moving starting from center coordinates of the second image and rearrange the taken image pixels into a rectangular image to generate a pattern image of the second image; the rearrangement unit is configured to take image pixels from the kidney border image while circularly moving along the kidney border image and rearrange the taken image pixels into a rectangular image to generate a pattern image of the kidney border image; and the rearrangement unit is configured to take image pixels from the third image and rearrange the taken images into a rectangular image to generate a pattern image of the third image.

2. An apparatus for AI-based automatic ultrasound diagnosis of liver steatosis, the apparatus comprising:
    an ultrasound probe sensor configured to acquire an ultrasound image from a patient;
    a region-of-interest extraction unit configured to extract images of one or more regions of interest from the ultrasound image;
    an image integration unit configured to combine the images of the images of the one or more regions of interest into one integrated image;
    a wavelet transform unit configured to decompose the integrated image into sub-band images by discrete wavelet transform;
    a darkness-to-shape transform kernel configured to transform the sub-band images into a shape-based sub-band image; and
    an artificial neural network trained on the shape-based sub-band image by deep learning,
    wherein the deep learning-trained artificial neural network is configured to automatically determine a grade of liver steatosis in the patient based on the ultrasound image of the patient received from the ultrasound probe sensor.

3. An apparatus for AI-based automatic ultrasound diagnosis of liver steatosis, the apparatus comprising:
    an ultrasound probe sensor configured to acquire an ultrasound image from a patient;
    a region-of-interest extraction unit configured to acquire images of one or more regions of interest helpful to diagnosis of liver steatosis from the ultrasound image;
    an image integration unit configured to combine the images of the one or more regions of interest into one integrated image;
    a darkness-to-shape transform kernel configured to transform the integrated image into a shape-based integrated image; and
    an artificial neural network trained on the shape-based integrated image by deep learning, wherein the deep learning-trained artificial neural network is configured to automatically determine a grade of liver steatosis in the patient based on the ultrasound image of the patient received from the ultrasound probe sensor,
    wherein the region-of-interest extraction unit comprises:
    an organ image database configured to store reference organ images as a reference for organ matching;
    a reference feature point storage unit configured to store feature points of the reference organ image (hereinafter referred to as "reference feature point");
    a feature point detection unit configured to extract matching feature points from the ultrasound image;
    a feature point pair generation unit configured to compare the reference feature point with respective matching feature points in patch images, which are formed around the respective matching feature points, to select patch images having a matching feature point with high similarity to the reference feature point, and generate a pair of feature points between the reference organ image and each of the selected patch images;
    an outlier detection unit configured to eliminate abnormal pairs of feature points among the generated pairs of feature points;
    a geometric parameter calculation unit configured to calculate geometric parameters required for registration of the resultant pairs of feature points, the geometric parameters comprising translation, rotation, and scaling; and
    an organ matching unit configured to acquire a registered patch image using the geometric parameters, calculate a cross-correlation coefficient between the registered patch image and the reference organ image, determine that a corresponding organ is located in a current patch image in the ultrasound image if the cross-correlation coefficient is greater than a predetermined threshold, extract an organ image region at a corresponding location, and transmit the organ image region to the image integration unit.

4. An apparatus for AI-based automatic ultrasound diagnosis of liver steatosis, the apparatus comprising:
    an ultrasound probe sensor configured to acquire an ultrasound image from a patient;
    a region-of-interest extraction unit configured to acquire images of one or more regions of interest helpful to diagnosis of liver steatosis from the ultrasound image;
    an image integration unit configured to combine the images of the one or more regions of interest into one integrated image;
    a darkness-to-shape transform kernel configured to transform the integrated image into a shape-based integrated image; and
    an artificial neural network trained on the shape-based integrated image by deep learning, wherein the deep learning-trained artificial neural network is configured to automatically determine a grade of liver steatosis in the patient based on the ultrasound image of the patient received from the ultrasound probe sensor,
    wherein the region-of-interest extraction unit comprises an artificial neural network configured to perform semantic segmentation on the ultrasound image to acquire a semantic segmented ultrasound image in which different organs of interest are labeled with different values or different colors for extraction of the images of the regions of interest,
    wherein the region-of-interest extraction unit is configured to:
    extract a region including a kidney and a liver from the ultrasound image by semantic segmentation and generate a first image including the extracted region;
    extract only a kidney region from the first image by semantic segmentation and generate a second image including the extracted kidney region;
    generate a kidney border image including a boundary between the first image and the second image;
    generate a third image including the remaining portion of the first image excluding the second image and the kidney border image; and
    transmit the second image, the kidney border image, and the third image to the image integration unit.

5. An apparatus for AI-based automatic ultrasound diagnosis of liver steatosis, the apparatus comprising:
    an ultrasound probe sensor configured to acquire an ultrasound image from a patient;
    a region-of-interest extraction unit configured to acquire images of one or more regions of interest helpful to diagnosis of liver steatosis from the ultrasound image;
    an image integration unit configured to combine the images of the one or more regions of interest into one integrated image;
    a darkness-to-shape transform kernel configured to transform the integrated image into a shape-based integrated image; and an artificial neural network trained on the shape-based integrated image by deep learning, wherein the deep learning-trained artificial neural network is configured to automatically determine a grade of liver steatosis in the patient based on the ultrasound image of the patient received from the ultrasound probe sensor, wherein the region-of-interest extraction unit comprises:

a wavelet frame unit configured to acquire a sub-band HL frame image, a sub-band LH frame image, and a sub-band HH frame image by wavelet frame transform of a reference organ image and the ultrasound image;

a feature point detection unit comprising feature point determination units configured to apply a feature point determination threshold to the respective sub-band frame images on a pixel-by-pixel basis and an overlapping pixel determination unit configured to detect overlapping pixels based on pixel-by-pixel multiplication between the sub-band frame images with respect to pixels having a value greater than the feature point determination threshold, the feature point detection unit configured to select overlapping pixels of the reference organ image acquired by the overlapping pixel determination unit as a reference feature point and select overlapping pixels of the ultrasound image acquired by the overlapping pixel determination unit as a matching feature point;

a feature point pair generation unit configured to compare the reference feature point with respective matching feature points in patch images, which are formed around the respective matching feature points, to select patch images having a matching feature point with high similarity to the reference feature point, and generate a pair of feature points between the reference organ image and each of the selected patch images;

an outlier detection unit configured to eliminate abnormal pairs of feature points among the generated pairs of feature points;

a geometric parameter calculation unit configured to calculate geometric parameters required for registration of the resultant pair of feature points, the geometric parameters comprising translation, rotation, and scaling; and an organ matching unit configured to acquire a registered patch image using the geometric parameters, calculate a cross-correlation coefficient between the reference organ image and the registered patch image, determine that a corresponding organ is located in a current patch image in the ultrasound image if the cross-correlation coefficient is greater than a predetermined threshold, extract an organ image region at a corresponding location, and transmit the organ image region to the image integration unit.

* * * * *